United States Patent [19]

Olness et al.

[11] Patent Number: 4,816,161
[45] Date of Patent: Mar. 28, 1989

[54] ISOPOTENTIAL AVAILABLE ION EXTRACTOR

[75] Inventors: Alan E. Olness, Morris, Minn.; Christopher Dahlem, Arcata, Calif.; Larry F. Bohlman, Correll, Minn.

[73] Assignee: The United States of America as represented by the Secretary of Agriculture, Washington, D.C.

[21] Appl. No.: 127,021

[22] Filed: Nov. 27, 1987

[51] Int. Cl.$^4$ .............................................. B01D 15/04
[52] U.S. Cl. .................................. 210/638; 210/669; 210/266; 210/282; 210/321.87; 422/61; 422/101; 436/178
[58] Field of Search ............... 210/638, 669, 266, 282, 210/289, 291, 321.71, 321.87, 500.23, 670, 681, 269, 281; 422/61, 101; 436/178

[56] References Cited

U.S. PATENT DOCUMENTS

| | | | |
|---|---|---|---|
| 3,240,067 | 3/1966 | Jongejan | 73/421 |
| 3,862,576 | 1/1975 | Pogorski | 73/432 R |
| 4,201,549 | 5/1980 | Tepe et al. | 436/178 |
| 4,298,475 | 11/1981 | Gartner | 210/266 |
| 4,303,610 | 12/1981 | Sardisco et al. | 422/61 |
| 4,636,307 | 1/1987 | Inoue et al. | 210/266 |
| 4,647,380 | 3/1987 | Dasgupta | 210/638 |

Primary Examiner—Ivars Cintins
Attorney, Agent, or Firm—M. Howard Silverstein; Curtis P. Ribando; John D. Fado

[57] ABSTRACT

A reusable extractor for obtaining a representative sample of the exchangeable ions from a complex heterogeneously saturated ion exchange system such as soil or other complex and colloidal matrices at various oxidation-reduction potentials without the need for costly extraction and purification steps. The extractor comprises a microporous dialysis membrane tube filled with cation- or anion-exchange resin beads. Extraction is effected by equilibrating homoionically saturated ion-exchange resin beads with a sample of the complex matrix under study. The extractor enables simple, rapid, multiple-element assays and provides the new capability of extracting exchangeable ions from stream, lake, and marine sediments in situ.

12 Claims, 2 Drawing Sheets

ISOPOTENTIAL AVAILABLE ION EXTRACTOR

BACKGROUND OF THE INVENTION

1. Field of the Invention

Chemical analyses of soils provide vital information for soil classification, plant nutrition, pollution control, and other soil-related matters. It is estimated that from 20,000 to 1,000,000 soil samples are analyzed annually, with the work approximately equally divided between publicly subsidized service laboratories and commercial laboratories. Most of the cost of this service is associated with extraction and purification steps required to prepare samples for analysis. This invention avoids completely the requirement of centrifugation and/or mechanical filtration while extraction a representative sample of the exchangeable ions.

2. Description of the Prior Art

The capability for ion exchange of both soils and synthetic resins has been recognized and documented extensively for several decades [Ion Exchange, McGraw-Hill Book Company, Inc., New York, NY, 1962; A Textbook of Soil Chemical Analysis, Chemical Publishing Company, Inc., New York, NY, 1972; Methods of Soil Analysis, Part 2, Chemical and Microbial Properties, American Society of Agronomy, Inc., and Soil Science Society of America, Inc., Madison, WI 1982]. Contemporary methods of determining the exchangeable/available ions in soil or complex and colloidal matrices rests almost exclusively on extensive use of mechanical technology (centrifuge, colorimeters, and mechanical filtration devices) and the chemical law of mass action wherein a salt solution that does not contain the chemical species of interest is introduced in such an overwhelming amount that the ion of interest is brought into solution. In most instances multiple element assays are limited because of various salt interactions. Contemporary methods preclude rapid and economical determination of the relative effects of oxidation-reduction potentials on the availability of trace elements in solution.

SUMMARY OF THE INVENTION

We have now discovered a system for use in the extraction of a representative fraction of exchangeable ions from complex matrices at various oxidation-reduction potentials. The system employs a reusable device comprising a microporous dialysis membrane tube filled with cation- or anion-exchange resin beads.

In accordance with this discovery, it is an object of the invention to provide an economical system for the rapid extraction of exchangeable ions from soils or sediments under ambient oxidation-reduction potentials.

It is also an object of the invention to provide a system that enables multiple-element assays without interference from ions present in salt solutions that are contemporarily used to extract soil samples for analysis.

A further object of the invention is to provide for examination of field-moist samples of soil under a range of redox conditions. Such examinations are quite difficult and tedious with present methods, which require drying of samples prior to analysis.

Another object of the invention is to avoid completely the contemporary requirement of centrifugation and/or mechanical filtration while extracting a representative sample of exchangeable ions from matrices.

It is also an object of the invention to provide the new capability of extracting exchangeable ions from stream, lake, and marine sediments in situ.

Other objects and advantages of this invention will become readily apparent from the ensuing description.

DETAILED DESCRIPTION OF THE INVENTION

Figure 1:
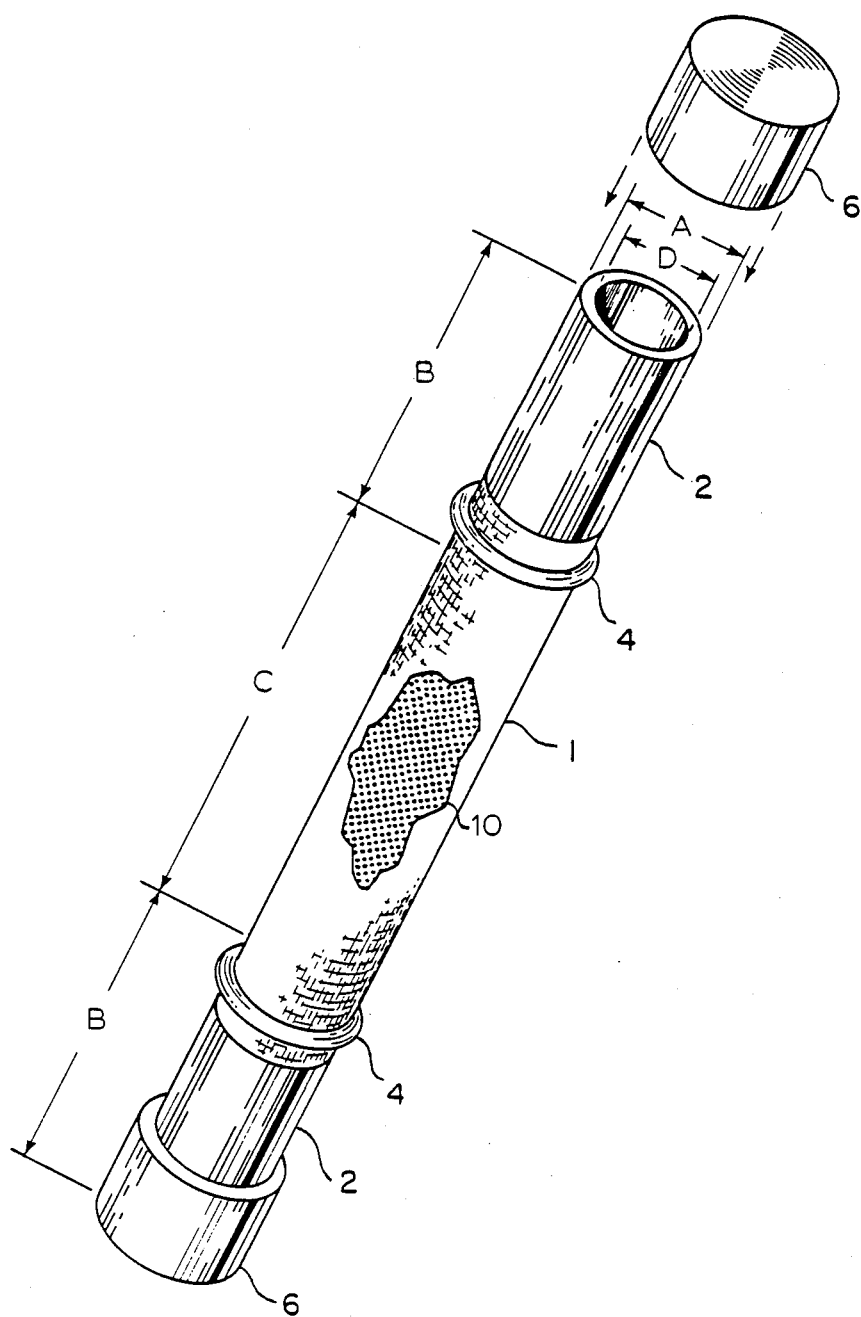
FIG. 1 is an overall perspective view of the assembled ion extractor of the invention.
Figure 2:
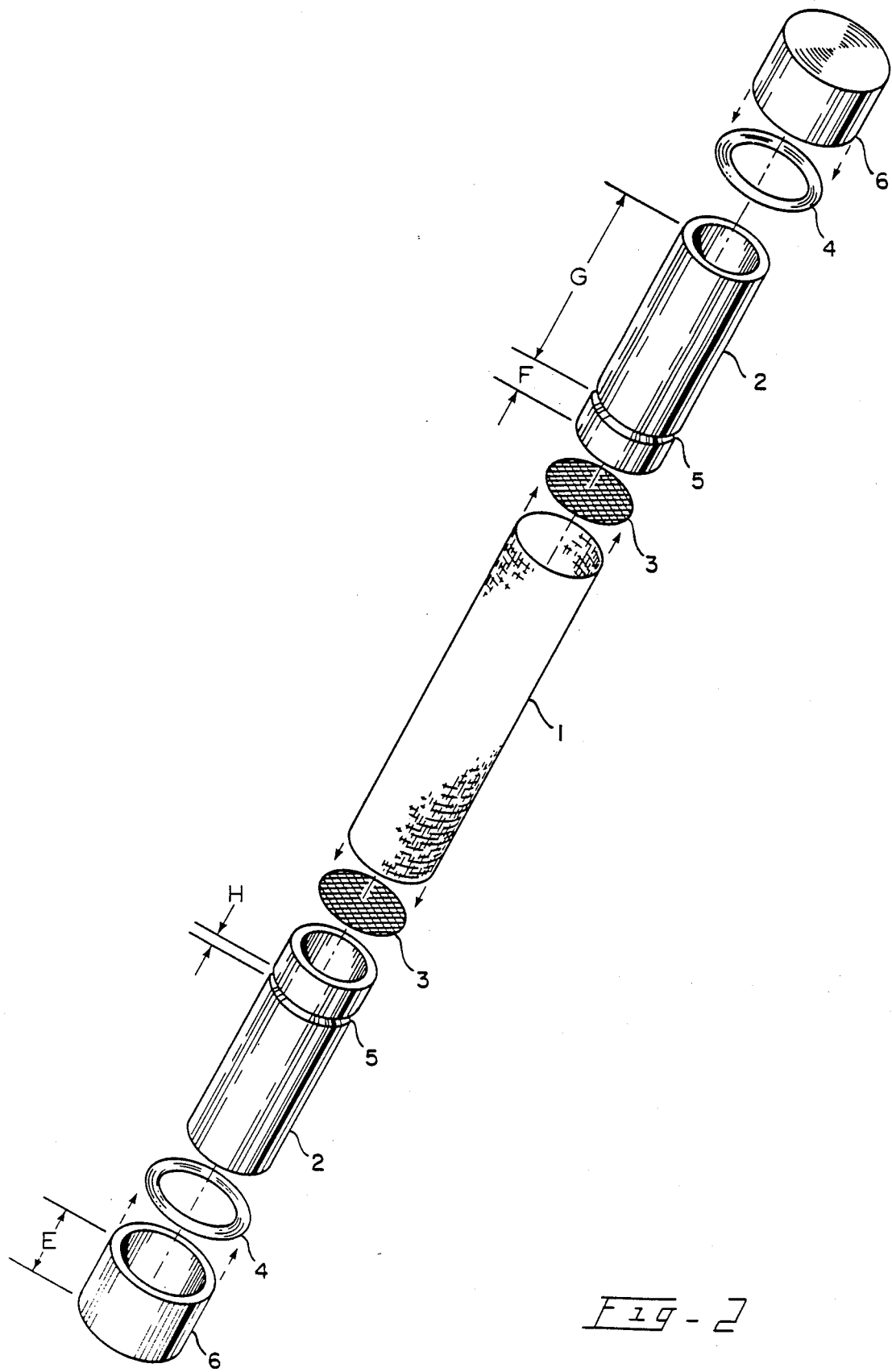
FIG. 2 is an exploded perspective view of support tubes for the dialysis membrane and tube enclosures.

The extraction of exchangeable ions from a matrix such as soil is based on the thermodynamic equilibrium of chemical potentials. A soil matrix is viewed as a mixture of cationic and anionic sites. The sum of all cation-exchange sites in a unit amount of soil constitutes the cation-exchange capacity (CEC) which is occupied by a variety of different cations. Anion-exchange sites are viewed in a similar manner. The mathematical description is given by:

$$CEC = \sum_{i=1}^{n} C_i n_i$$

where
 $c_i$ = the $i^{th}$ cation species
 $n_i$ = the number of $C_i$ ions in a unit amount of soil.

When a homoionically saturated exchange system is equilibrated with the soil, a proportionate amount of each cation species on the soil exchanges with an ion carried by the exchange system. The exchange process continues until equilibrium of the chemical potentials of each ion species in the soil and the exchange system is attained. The extraction system is then eluted with purified acid to effect an exchange of hydrogen ions for the adsorbed cations and recharge the exchange systems by returning it to its original homoionically saturated state. Eluted cations are determined by appropriate methods. Anion exchange is effected in similar manner using an appropriately prepared anion-exchange resin.

Referring to the drawings, the reusable, isopotential, available ion extractor described herein comprises cation- or anion-exchange resin beads 10 retained within microporous dialysis membrane tube 1 such that the resin beads can be homoionically saturated, equilibrated, discharged, and regenerated without disassembly. An example of a suitable dialysis membrane is regenerated cellulose tubing having a 12,000 to 14,000 molecular weight cutoff. Beads 10 are retained in the flexible film dialysis tube 1 by support tubes 2 which each have a screen 3 of an appropriately-sized mesh attached to the interior end by means of a suitable adhesive. Support tubes 2 may be constructed of glass, plastic, or other comparatively inert and nonporous material substantially free of extractable ions which would interfere with analytical determinations. Screens 3 are preferably constructed from nylon or some other non-corrosive material. Retainer rings 4 for the dialysis membrane may consist of commercially available rubber "O" rings, rubber bands, or heat-shrinkable tubing. Groove 5 provides seating for retainer ring 4.

The extractor is assembled by first fitting the screens 3 onto the medial ends of the support tubes 2. One end of the dialysis membrane tube 1 is then slipped over one of the support tubes and secured in place with retainer ring 4 positioned in seating groove 5. After filling the tube 1 with beads 10, the free end of the tube is likewise fitted over the other support tube 2 and secured by a retainer ring 4. End caps 6 are put on the exterior (lateral) ends of support tubes 2 during equilibration in a soil suspension to prevent admission of soil. The caps 6 are preferably designed to be held in place by frictional engagement with the outer surface of tubes 2; or alternatively, the respective members can be equipped with mating threads.

When preparing an extractor for extraction of cations, the beads are homoionically saturated by leaching with a high purity acid, such as 1N nitric acid or hydrochloric acid. This is preferably accomplished by flushing acid through the extractor from one end to the other with end caps 6 removed. The extractor is then rinsed with deionized water until all excess hydrogen ions are removed. At this point, the pH will be 5.0 or more and the resistance of the eluate will be at least about 500,000 ohms. Once saturated, the extractor can be stored by submerging in deionized water ($1 \times 10^6$ ohms or higher resistance) to prevent dehydration of the dialysis membrane and contamination of the resin with trace amounts of foreign ions.

Extractors are similarly prepared for anionic exchange. In fact, by flushing a positively-charged anion-exchange resin with nitric acid, the nitrate ions will saturate the exchange sites and will be available for displacement by anionic moieties in the soil sample.

At the time of use, the extractor is placed in an aqueous suspension of the soil sample to be analyzed. For best results, the soil is suspended at a level of about 12–40% weight/volume. Equilibration should proceed at a temperature in the range of about 0.5° to 4° C. to minimize microbial activity. Separate extractors charged for cation exchange and anion exchange can be simultaneously placed in the same soil suspension.

The exchange ratio, which is the ion-exchange capacity of the soil divided by the ion-exchange capacity of the extractor should be greater than 10 in order to minimize exchange ion effects. When, for example, hydrogen ions on the resin are being exchanged for cations in the soil, there is a tendency for the soil pH to be depressed. At exchange ratios greater than 10, this effect becomes negligible.

After equilibration with exchangeable ions in the soil sample, the extractor is removed from the soil suspension, rinsed with deionized water to remove soil particles adhering to the outer surface, and flushed with deionized water to remove excess dissolved salts from the resin. Thereafter, the resin is eluted with acid in order to leach the exchanged ions from the exchange sites and to return the resin to a homoionically saturated exchange state for subsequent reuse. The sample leachate (usually 10 ml or less) is collected in tubes. After appropriate preparation, the sample is analyzed for concentrations of constituents of interest by known methods such as atomic absorption spectroscopy, and inductively coupled plasma emission spectroscopy.

The extraction system described herein is capable of functioning over a virtually unlimited range of soil conditions. By permitting analysis of field-moist soil samples without prior drying, the system avoids elevation of the oxidation-reduction potential of the sample and the concomitant interference with determination of elements such as iron and manganese. A broad range of cations and anions can be used to saturate the cation- and anion-exchange resins although monovalent ions are preferred. Alkalis such as hydroxide, carbonate nd bicarbonate should be avoided when a regenerated cellulose membrane is used, because of their tendency to interfere with the permeability of these membranes. If such alkalis are required in the exchange system, damage to the dialysis membrane can be minimized by charging and rinsing the resin before loading it into the extractor.

The following examples are intended only to further illustrate the invention and are not intended to limit the scope of the invention which is defined by the claims.

EXAMPLE

Extractors were constructed in accordance with the preceding description using the following dimensions (in mm): A, 6; B, 30; C, 30; D, 3; E, 10; F, 6; G, 24; and H, 0.5. The membrane tube 1 was fashioned from "Spectra/Por 4" regenerated cellulose tubing measuring 25 mm wide in the dry, flattened state, 0.0008 mm thickness, and 12,000–14,000 molecular weight cutoff. These extractors were evaluated for efficacy of extracting a representative fraction of exchangeable ions in soil. For example, A Tara sil was equilibrated for 1 week at redox potentials of −246 and 569 mv, respectively; the reduced condition was obtained by microbial respiration. Inductively coupled plasma methods were used to analyze the extracts; the extract volume was 10 ml. The results are reported in Table I below. Of 18 elements surveyed, 11 different elements were found in a single extract. Several elements were affected by change in the redox potential. Advantages of the method are: (1) extracts are obtained without centrifugation, (2) analyzable extracts are obtained without filtration, and (3) volume of chemical reagents used is much less than that required for conventional methods. The method appears suitable for application to soil classification, soil-plant nutrition, sediment, pollution, and particularly to studies of effects of redox potential on soil chemical mobility.

It is understood that the foregoing detailed description is given merely by way of illustration and that modification and variations may be made therein without departing from the spirit and scope of the invention.

TABLE I

| | | Sample size (g) | | |
| --- | --- | --- | --- | --- |
| | | 3 | 6 | 10 |
| Redox potential (mv) | Element | $\mu$g/ml[a] | | |
| 569 | Phosphorus | 3.67 | 3.96 | 3.68 |
| | Potassium | 15.6 | 19.9 | 21.0 |
| | Calcium | 59.9 | 107.2 | 83.8 |
| | Magnesium | 28.9 | 46.8 | 36.0 |
| | Aluminum | — | 0.11 | 0.17 |
| | Iron | 0.07 | 0.07 | Tr |
| | Sodium | 6.9 | 8.9 | 8.8 |
| | Manganese | 0.94 | 1.63 | 2.07 |
| | Zinc | 0.12 | 0.10 | 0.06 |
| | Copper | — | — | — |
| | Boron | — | — | — |
| | Lead | — | — | — |
| | Nickel | 0.05 | Tr | Tr |
| | Chromium | — | — | — |
| | Silicon | 0.12 | 0.07 | 0.06 |
| | Molybdenum | — | — | — |
| | Cobalt | — | — | — |
| | Cadmium | — | — | — |
| −246 | Phosphorus | nd | — | — |
| | Potassium | 0.35 | 0.61 | 0.60 |
| | Calcium | 369.0 | 365.0 | 346.0 |
| | Magnesium | 90.9 | 78.2 | 74.0 |

TABLE I-continued

| Redox potential (mv) | Element | Sample size (g) | | |
|---|---|---|---|---|
| | | 3 | 6 | 10 |
| | | μg/ml[a] | | |
| | Aluminum | 0.94 | 0.81 | 0.78 |
| | Iron | 51.2 | 40.2 | 45.4 |
| | Sodium | — | — | — |
| | Manganese | 12.8 | 14.9 | 16.2 |
| | Zinc | nd | 0.45 | 0.18 |
| | Copper | 0.05 | Tr | Tr |
| | Boron | 0.06 | Tr | Tr |
| | Lead | — | — | — |
| | Nickel | 0.20 | 0.18 | 0.14 |
| | Chromium | Tr | Tr | Tr |
| | Silicon | 0.36 | 0.14 | 0.21 |
| | Molybdenum | Tr | — | Tr |
| | Cobalt | 0.10 | 0.11 | 0.09 |

[a]Concentrations are relative values. Abbreviations are as follows:
Tr = Trace (value on the order of blank),
nd = no determination, and
— = not detectable. Blank values have been subtracted.

We claim:

1. A device for extracting a representative fraction of exchangeable ions from an aqueous suspension of soil, sediment, or other complex matrix having exchangeable ions comprising a microporous dialysis membrane tube containing an ion exchange resin and a pair of nonporous support tubes, one support tube secured to each end of said dialysis membrane tube, wherein the interior of each support tube is separated from the resin by a mesh having openings adapted to allow fluid flow through said mesh while retaining the resin.

2. The device of claim 1 wherein the resin is a cation-exchange resin.

3. The device of claim 1 wherein the resin is an anion-exchange resin.

4. The device of claim 1 wherein the support tubes are constructed from a rigid polymeric plastic.

5. The device of claim 1 further comprising a pair of end caps adapted for sealing opposing ends of said device.

6. A method for extracting a representative fraction of exchangeable ions from an aqueous suspension of soil, sediment, or other complex matrix having exchangeable ions by means of a device comprising a microporous dialysis membrane tube containing an ion exchange resin and a pair of nonporous support tubes, one support tube secured to each end of said dialysis membrane tube, wherein the interior of each support tube is separated from the resin by a mesh having openings adapted to allow fluid flow through said mesh while retaining the resin, and wherein the opposing ends of said device are sealed with a pair of removable end caps, said method comprising:
  a. homoionically saturating the ion exchange resin;
  b. equilibrating the resin by submerging the device in the aqueous suspension of the matrix;
  c. removing the end caps and eluting the equilibrated resin by passing a suitable eluent through the interior of the device to obtain an eluate containing said ions; and
  d. collecting the eluate.

7. The method as described in claim 6 wherein the ion exchange capacity of the matrix is at least 10 times that of the resin.

8. The method as described in claim 6 wherein the resin is a cation-exchange resin.

9. The method as described in claim 6 wherein the resin is an anion-exchange resin.

10. The method as described in claim 6 wherein the matrix is a soil.

11. The method as described in claim 10 wherein the soil is in a reduced state.

12. The method as described in claim 10 wherein the soil is in an oxidized state.

* * * * *